United States Patent
Chism, II

(10) Patent No.: US 7,239,392 B2
(45) Date of Patent: *Jul. 3, 2007

(54) POLARIZATION MODULATION PHOTOREFLECTANCE CHARACTERIZATION OF SEMICONDUCTOR ELECTRONIC INTERFACES

(75) Inventor: William W. Chism, II, Austin, TX (US)

(73) Assignee: Xitronix Corporation, Austin, TX (US)

( * ) Notice: Subject to any disclaimer, the term of this patent is extended or adjusted under 35 U.S.C. 154(b) by 195 days.

This patent is subject to a terminal disclaimer.

(21) Appl. No.: 11/098,764

(22) Filed: Apr. 4, 2005

(65) Prior Publication Data

US 2006/0098198 A1 May 11, 2006

Related U.S. Application Data

(63) Continuation-in-part of application No. 10/847,202, filed on May 17, 2004, now Pat. No. 6,963,402.

(60) Provisional application No. 60/558,829, filed on Apr. 5, 2004, provisional application No. 60/472,687, filed on May 22, 2003.

(51) Int. Cl.
*G01J 4/00* (2006.01)
(52) U.S. Cl. ...................... 356/369; 356/364; 356/365; 356/366; 356/367; 356/368
(58) Field of Classification Search ................ 356/432, 356/72, 128, 364–369, 445–448; 250/225, 250/559.22
See application file for complete search history.

(56) References Cited

U.S. PATENT DOCUMENTS

| | | | |
|---|---|---|---|
| 3,982,207 A | | 9/1976 | Dingle et al. |
| 4,652,757 A | * | 3/1987 | Carver ................. 250/360.1 |
| 4,750,822 A | | 6/1988 | Rosencwaig et al. |
| 4,931,132 A | | 6/1990 | Aspnes et al. |
| 5,501,637 A | | 3/1996 | Duncan et al. |
| 5,536,936 A | | 7/1996 | Drevillon et al. |
| 5,757,671 A | | 5/1998 | Drevillon et al. |
| 6,195,166 B1 | | 2/2001 | Gray et al. |
| 6,400,449 B2 | * | 6/2002 | Maris et al. .................. 356/72 |
| 6,963,402 B2 | * | 11/2005 | Chism, II .................. 356/369 |
| 2002/0027704 A1 | * | 3/2002 | Kobayashi et al. ...... 359/341.1 |

OTHER PUBLICATIONS

International Search Report issued on Mar. 10, 2005 for PCT/US04/15622.
Airaksinen et al, "Photoreflectance study of photovoltage effects in GaAs diode structures," Appl. Phys. Lett., 60:17, 2110-2112, Apr. 27, 1992.
Aspnes, "Characterization of semiconductors and semiconductor structures by optical techniques/optical properties of materials and structures," SPIE, Oct. 1990.

(Continued)

*Primary Examiner*—Gregory J. Toatley, Jr.
*Assistant Examiner*—Tri Ton
(74) *Attorney, Agent, or Firm*—Vinson & Elkins LLP

(57) ABSTRACT

A polarization modulation photoreflectance technique has been developed for optical characterization of semiconductor electronic interfaces. By using a laser source in conjunction with polarization state modulation, a polarization modulation spectroscopy technique may be used to characterize the optical response of semiconductor materials and structures. Disclosed methods and instruments are suitable for characterization of optical signatures of electronic interfaces, including characterization of electric fields at semiconductor interfaces.

32 Claims, 15 Drawing Sheets

OTHER PUBLICATIONS

Aspnes, "Observation and analysis of epitaxial growth with reflectance-difference spectroscopy," Materials Science and Engineering B30, 109-119, 1995.

Glembocki et al., "Photoreflectance characterization of interband transitions in GaAs/AlGaAs multiple quantum wells and modulation-doped heterojunctions," Appl. Phys. Lett., 46:10, 970-972, May 15, 1985.

Klar et al., "Photomodulated reflectance study of $In_x Ga_{1-x}$ As/BaAs/AlAs microcavity vertical-cavity surface emitting laser structures in the weak-coupling regime: The cavity/ground-state-exciton resonance," Physical Review B, 59:4, 2894-2901, Jan. 15, 1999.

Miller et al., "Large room-temperature optical nonlinearity in GaAs/$Ga_{1-x} Al_x$as multiple quantum well structures," Appl. Phys. Lett., 41:8, 679-681, Oct. 15, 1982.

Pollak et al., "Room temperatureS, contactless electromodulation investigation of wafer-sized quantum well laser structure," SPIE 2693, 455-466, 1996.

Seraphin et al., "Franz-keldysh effect above the fundamental edge in germanium," Physical Review Letters, 14:5, 138-140, Feb. 1, 1965.

Shay, "Photoreflectance line shape at the fundamental edge in ultrapure GaAs," Physical Review B, 2:4, 803-807, Aug. 15, 1970.

Weiner et al., "Strong polarization-sensitive electroabsorption in GaAs/AlGaAs quantum well waveguides," Appl. Phys. Lett., 47:11, 1148-1150, Dec. 1, 1985.

Zheng et al., "Photoreflectance and the seraphin coefficients in quantum well structures," SPIE, 946, 43-47, 1988.

\* cited by examiner

POLARIZATION MODULATION PHOTOREFLECTANCE CHARACTERIZATION OF SEMICONDUCTOR ELECTRONIC INTERFACES

CROSS-REFERENCE TO RELATED APPLICATIONS

The present application is a continuation-in-part of U.S. application Ser. No. 10/847,202, filed May 17, 2004 now U.S. Pat. No. 6,963,402, and also claims benefit of U.S. Provisional Patent Application Ser. No. 60/558,829, filed on Apr. 5, 2004, which are incorporated herein in their entireties by reference.

FIELD OF THE INVENTION

The present invention relates to optical characterization of semiconductor electronic interfaces and, more particularly, to the use of polarization modulation photo-reflectance to characterize the physical properties of the electronic interface.

BACKGROUND OF THE INVENTION

High sensitivity optical measurement techniques are required in the fabrication of electronic and optoelectronic devices. The manufacture of semiconductor devices typically begins with a large substrate wafer of semiconductor material, and a large number of semiconductor devices are formed in each wafer. Because the device manufacturing steps are time consuming and expensive, it is important to the manufacturing process of such semiconductor devices that the physical characteristics of semiconductor device structures only vary within a small process window. In order to attain the earliest possible feedback during production, it is necessary to non-destructively characterize the physical properties of device structures before the device is complete. Importantly, the physical phenomena which governs electronic and optoelectronic device operation often occurs at interfaces. For example, the transistor structure generally comprises a "channel" region near a semiconductor-insulator interface, wherein the electrical properties of the channel are controlled by an externally applied voltage. In production, it is also necessary that the measurement be entirely non-destructive, a requirement which strongly favors the use of optical techniques. The optical signatures of interfacial electric fields occur in the vicinity of strong interband transition features such as the band gap, and typically have small amplitudes, in some cases as small as one part in $10^6$. Typical values of the photo-reflectance signal from semiconductor electronic interfaces range in amplitude from $\sim 10^{-2}$–$10^{-5}$ (Pollack, 1994; Shay 1970). Unfortunately, widely available optical techniques such as ellipsometry or reflectance do not have the sensitivity required to observe signatures of electronic interfaces. However, these signatures necessarily occur in the optical wavelength range, since semiconductor interband transitions occur in the ~1-5 eV range. Thus, high sensitivity optical techniques are needed in the extraction of semiconductor interfacial electronic signatures.

The requirement for high sensitivity may be met by a proven class of optical techniques known as modulation spectroscopy techniques. Modulation spectroscopy techniques such as "electro-reflectance" and "photo-reflectance" have exhibited sensitivity to differential changes in reflectivity as small as $10^{-7}$. Of the modulation spectroscopy techniques, photo-reflectance is best suited for use in the fabrication of electronic and optoelectronic devices, as it is nondestructive and only requires the sample have a reflecting surface (Aspnes, 1980). The conventional photo-reflectance configuration employs a diode laser pump beam to induce small periodic changes in electron-hole populations. Amplitude modulation of the pump beam is conventionally accomplished with an optical chopper, or by fixturing a polarizer at the output of a phase modulator. A second optical beam, coincident with the modulated pump beam is then used to monitor small sample reflectivity changes using phase locked detection. Thus, the conventional photo-reflectance configuration is a realization of electro-modulation, wherein the electric field is induced by the space charge separation field of the electrons and holes (Pollack, 1996).

A primary problem with conventional photo-reflectometers is that they do not use a probe beam containing wavelengths suitable for characterization of electric fields at semiconductor interfaces. Importantly, modulation of internal electric fields produces sharp derivative-like spectral features near strong interband transitions, known as "critical points," in the semiconductor band structure (Pollack, 1994). Thus, by using a probe beam with wavelength nearby to at least one critical point in the band structure of the semiconductor structure, photo-reflectance information may be used to characterize the signatures of electronic interfaces.

Another problem with conventional photo-reflectometers is that they do not employ a polarization modulation technique to induce changes in the optical response of the electronic interface. Generally, the optical response of a semiconductor electronic interface is anisotropic with respect to polarization vector. In particular, the optical response depends on the amplitude and direction of the induced electric field (Keldysh, 1970). For example, light polarized in the plane of an electronic interface can accelerate free carriers, producing a sharp third-derivative photoreflectance lineshape, whereas light polarized normal to the plane of a quantum cannot accelerate carriers and typically results in a first-derivative lineshape (Aspnes, 1980). Thus, by using polarization state modulation of the pump beam, and introducing the laser beam at a non-zero angle with respect to the surface normal, an anisotropic optical response may be induced at the electronic interface.

Another problem with common photo-reflectometers is they lack a spectroscopic probe beam (Rosencwaig, 1985, Borden, 2000). Since the photoreflectance signal is obtained at only a single wavelength, the spectral position of critical points, such as those associated with internal electric fields and/or semiconductor band structures, cannot be determined. Thus, while commercial photo-reflectometers may be useful in correlation to electronic carrier densities or thermal effects, these cannot usefully determine internal electric fields or semiconductor band structures.

Thus, while conventional photo-reflectometers and optical spectrometers may be suitable for the particular purpose to which they address, they are not well suited for the characterization of the optical response of semiconductor electronic interfaces. In particular, they do not use a probe beam containing wavelengths suitable for characterization of electric fields at semiconductor interfaces. Moreover, although conventional photo-reflectometers may use a laser pump beam with sufficient power and focusing to create electric field modulation inside the sample, this pump is not polarization modulated so as to induce anisotropic optical responses associated with semiconductor electronic interfaces. The polarization modulation feature of the technique also allows ellipsometric characterization of the semiconductor film structure. Additionally, although conventional reflectance difference spectroscopy has been accomplished using polarization modulation, it has been implemented at normal incidence, providing minimal sensitivity to electronic interfaces. Also, conventional reflectance difference spectroscopy uses lower laser powers.

In these respects, the polarization modulation photo-reflectometer according to the present disclosure substantially departs from the conventional concepts and designs of the prior art, and in so doing, provides an apparatus primarily developed for the characterization of optical signatures of electronic interfaces, including photo-reflectance features at the band edge or other direct or indirect critical points in the band structure.

SUMMARY OF THE INVENTION

In view of the foregoing disadvantages inherent in the known types of optical spectroscopy now present in the art, the present disclosure provides a new polarization modulation photo-reflectometer construction wherein the same can be utilized for the characterization of optical signatures of electronic interfaces, including characterization of electric fields or mechanical strain at semiconductor interfaces.

The present disclosure, which will be described subsequently in greater detail, provides a new polarization modulation photo-reflectometer that has many of the advantages of the optical spectroscopy mentioned heretofore and many novel features that result in a new polarization modulation photoreflectometer which is not anticipated, rendered obvious, suggested, or implied by any of the prior art, either alone or in any combination thereof.

The underlying principle of the polarization modulation photoreflectance technique is to characterize photo-reflectance signals due to the optical response of electronic interfaces. The presence of an electronic interface produces sharp features in the photoreflectance signal. The polarization modulation photoreflectance technique provides the ability to generate and record photoreflectance information associated with electronic interfaces. To attain this, the present disclosure generally comprises a diode laser pump, a laser controller and power supply, a phase modulator with a function generator, a probe light source, an optical system, a sample, a photoreceiver, a signal conditioner, and a computer with measurement and system control software. The laser power is approximately 15 mW, with wavelength above the absorption edge of the semiconductor material. The laser controller is controlled by the computer and may perform power and/or wavelength scans. The laser beam polarization state is modulated by a phase modulator driven by an external function generator. The laser beam and a probe light beam are spatially overlapped at a focal spot on the sample and reflected light is collected by the optical system. The probe beam is directed to a photoreceiver which generates an electrical current proportional to the input intensity. The photoreceiver output comprises the AC signal at the modulation frequency and the DC photocurrent. The AC signal is divided by the DC signal, which provides normalization of the probe light intensity. The AC signal is then proportional to the differential change in reflectivity. A lock-in amplifier with reference frequency from the phase modulator then records the photoreceiver output. The computer controls the laser and records experimental photocurrents from the lock-in amp. Thus photoreflectance wavelength information related to the optical response of electronic interfaces is acquired.

Ellipsometric information contained in the reflected pump beam may also be analyzed by using a polarizer, known as an "analyzer," to produce an amplitude modulation of the pump laser intensity. The amplitude modulated pump beam is directed to a photoreceiver which generates an electrical current proportional to the input intensity. The photoreceiver output comprises the AC signal at the modulation frequency and the DC photocurrent. The AC signal is a sum of odd and even harmonics of the phase modulation frequency. The amplitude of these harmonics contain the ellipsometric parameters $\Psi$ and $\Delta$. The AC signal is divided by the DC signal, which provides normalization of the pump intensity. A lock-in amplifier with reference frequency from the phase modulator then records the photoreceiver output. The computer controls the laser and records experimental photocurrents from the lock-in amp. Thus, the pump beam is configured independently as a polarization modulation ellipsometer.

The semiconductor materials that are the subject of the present disclosure may be any semiconductor materials containing electronic interfaces, and may include, but are not limited to Group III-V semiconductor materials or Group II-IV semiconductor materials. In certain embodiments such materials may include gallium arsenide, gallium aluminum arsenide, gallium nitride, aluminum nitride, gallium phosphide, indium gallium arsenide, indium antimonide, or combinations thereof, or they may include silicon, germanium, silicon germanium, carbon, silicon carbide, zinc oxide, zinc sulfide, cadmium sulfide, cadmium selenide, or combinations thereof.

There has thus been outlined, rather broadly, the more important features of the disclosure in order that the detailed description thereof may be better understood, and in order that the present contribution to the art may be better appreciated. There are additional features of the disclosure that will be described hereinafter.

In this respect, before explaining at least one embodiment of the disclosure in detail, it is to be understood that the disclosure is not limited in its application to the details of construction and to the arrangements of the components set forth in the following description or illustrated in the drawings. The disclosure is capable of other embodiments and of being practiced and carried out in various ways. Also, it is to be understood that the phraseology and terminology employed herein are for the purpose of the description and should not be regarded as limiting. This disclosure may be embodied in the form illustrated in the accompanying drawings, attention being called to the fact, however, that the drawings are illustrative only, and that changes may be made in the specific construction illustrated.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

DETAILED DESCRIPTION

The following discusses use of the polarization modulation photoreflectance (PMPR) technique for characterization of electronic interfaces. It is understood that the PMPR technique of the present drawings and descriptions may be used to analyze any semiconductor material, the discussion of electronic interfaces considered to be exemplary only and in no way limiting in scope.

Figure 1:
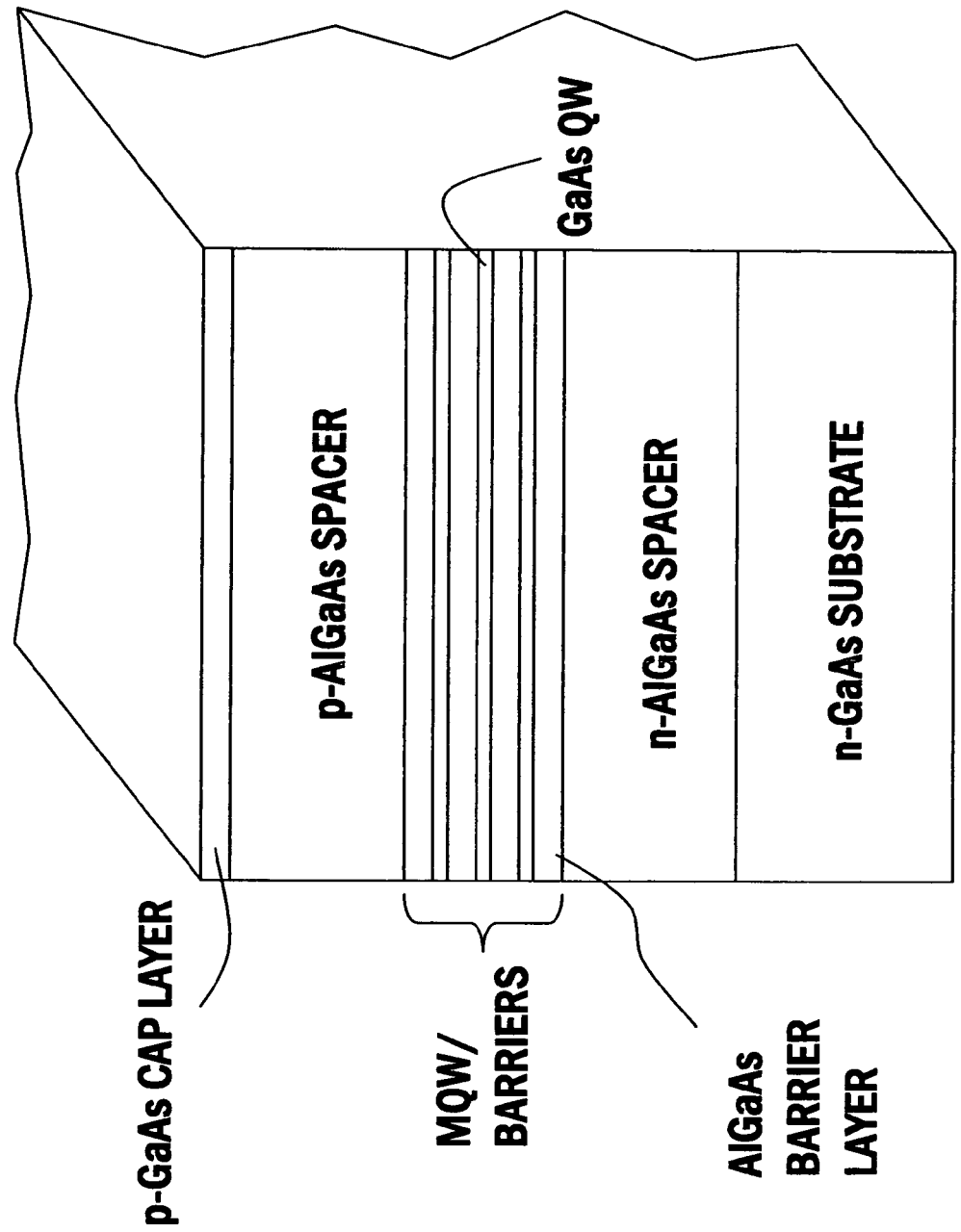
FIG. 1 illustrates an exemplary semiconductor material containing electronic interfaces that may be analyzed using the photo-reflectance technique of the present disclosure.

Turning now descriptively to the drawings, in which similar reference characters denote similar elements throughout the several views, FIG. 1 contains, in an exaggerated view, an exemplary electronic interface test structure that may be characterized using the polarization modulation photo-reflectance technique of the present disclosure. The electronic interface test structure, which may be grown using molecular beam epitaxy, comprises a negatively doped gallium arsenide (GaAs) semiconductor substrate upon which is grown a negatively doped aluminum gallium arsenide (AlGaAs) "spacer" layer of ~94.5 nanometer thickness. An undoped barrier layer comprising AlGaAs is grown on the spacer layer. Then a multiple quantum well section comprising a number of periods of GaAs quantum wells and AlGaAs barrier layers is grown on the first barrier layer. In an exemplary embodiment, individual quantum wells may comprise a thickness of approximately 7.4 nanometers, and barriers may comprise a thickness of approximately 7.4 nanometers. A second confinement layer is grown on the multiple quantum well section. The electronic interface test structure further comprises an additional AlGaAs spacer layer of approximately 94.5 nanometer thickness, followed by a thin GaAs capping layer.

Figure 2:
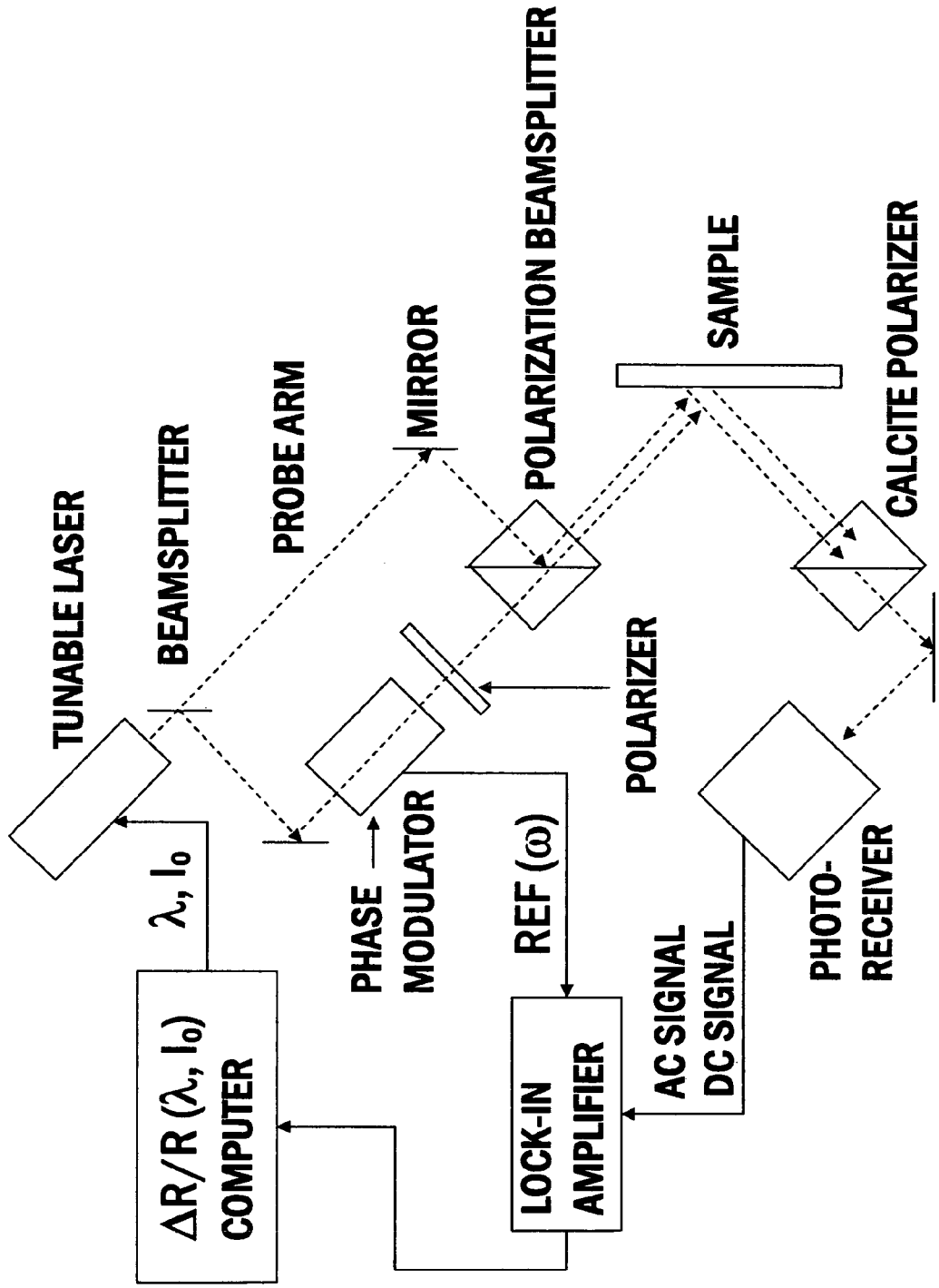
FIG. 2 contains an arrangement of a polarization modulation photo-reflectivity apparatus which may be used to provide photo-reflectance characterization in accordance with present disclosure.

In accordance with the arrangement of the present disclosure as shown in FIG. 2, polarization modulation photo-reflectance may be used to measure the reflected spectra from an electronic interface test structure in order to characterize the properties of the electronic interface, and importantly, establish the energy of optical transitions in the electronic interface, and establish the profile of the dielectric function in the vicinity of such transitions. By introducing the laser beam at a non-zero angle of incidence with respect to the electronic interface layers, a component of polarization perpendicular to the plane of the layers is realized. For polarization in the plane of the electronic interface, acceleration of free carriers may occur, whereas for components perpendicular to the interface layers, no acceleration is possible. As shown in FIG. 2, the polarization modulation photo-reflectance arrangement comprises a tunable diode laser, a laser controller, a beamsplitter, a phase modulator with a function generator, a polarizer, a polarizing beamsplitter, an optical system, a sample, a photoreceiver, a lock-in amplifier, and a computer with measurement and system control software.

Figure 3:
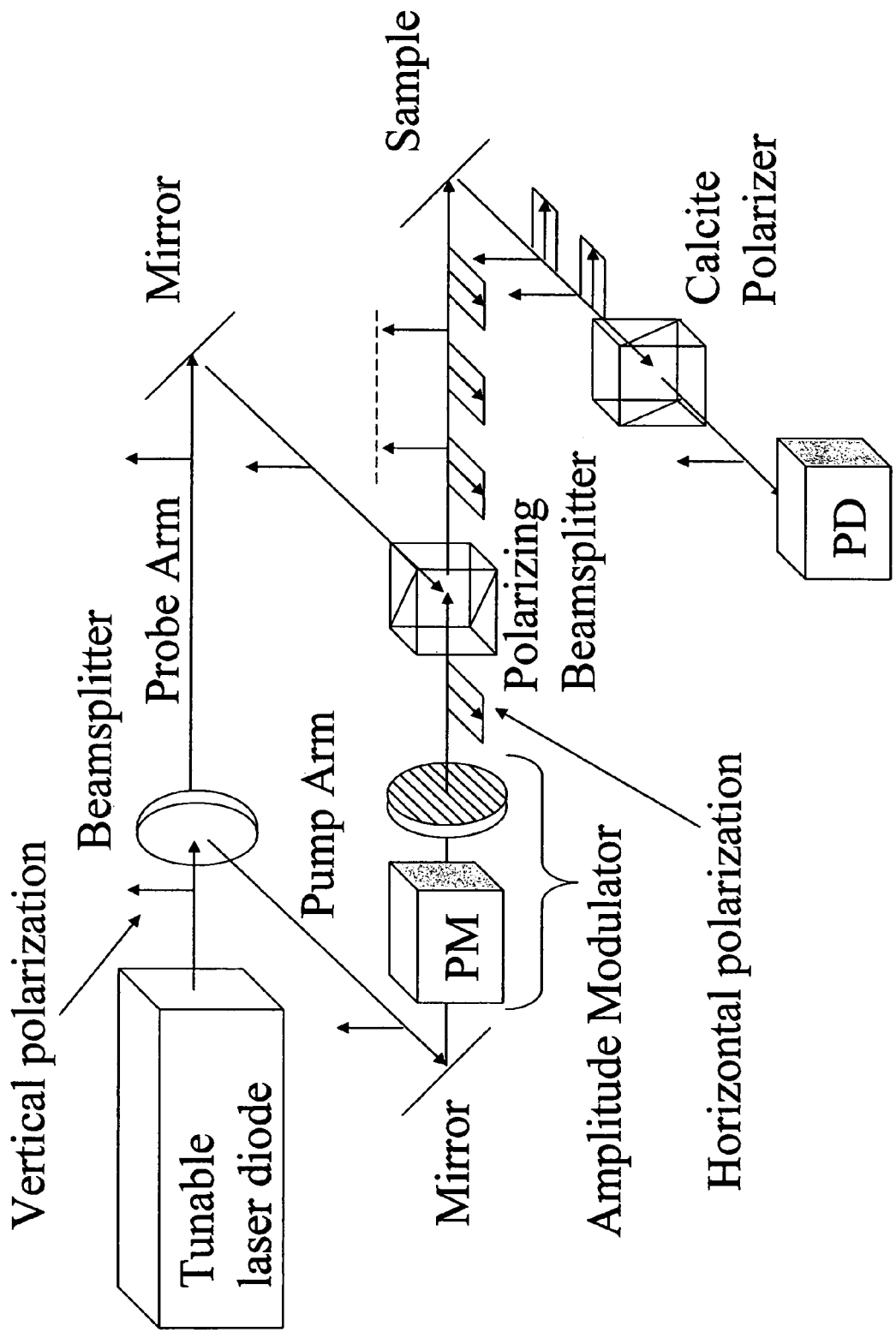
FIG. 3 is a schematic representation of a polarization state through a preferred optical system.

In certain embodiments the laser diode is an external cavity tunable laser diode with center wavelength of approximately 844 nm and tunable range of approximately 20 nanometers. Laser embodiments include external cavity tunable diode lasers emitting in the UV-NIR wavelength range (200-1700 nm). The laser power is approximately 15 mW. However, laser embodiments include lasers operating at powers of approximately 0.5 mW or above. The laser controller is a programmable power source compatible with the laser diode and may be controlled by the computer. The laser beam is directed to a beamsplitter, where the beam is separated into a pump and a probe arm. The pump arm is directed through the phase modulator where its polarization state is modulated. In an exemplary embodiment the phase modulator is an electro-optic modulator based on the Pockel's effect with resonant frequency of approximately 20 MHz driven by an external function generator. Embodiments also include broadband phase modulation, DC bias operation, and photo-elastic modulation. The pump beam is then passed through a polarizer, which produces an amplitude modulation. The pump and probe arms are then made collinear through the use of a polarizing beamsplitter. This yields a single beam wherein the amplitude modulated pump has linear polarization with direction perpendicular to the probe polarization. The beam is then focused onto the sample surface at an angle of incidence of approximately 65°. The optical system comprises various optical elements including focusing and collimation lenses, and mirrors. All optical elements are matched to the laser source wavelength. FIG. 3 shows the polarization state of the laser beam as it passes through the optical system. The pump polarization is aligned either parallel or perpendicular to the plane of incidence. In either alignment, the pump polarization state remains linearly polarized after reflection from the sample, allowing the pump light to be effectively eliminated from the beam with the use of a calcite polarizer. Once the beam is reflected from the sample surface, it has sources of amplitude modulation from the amplitude modulated pump "channel," and on the probe channel from any induced change in the semiconductor optical response. The calcite polarizer is oriented to minimize the transmission of the pump beam. This also provides maximal transmission of the probe beam, which contains the photoreflectance signal. Any residual pump light produces a constant or sloping background which may be removed.

Figure 4:
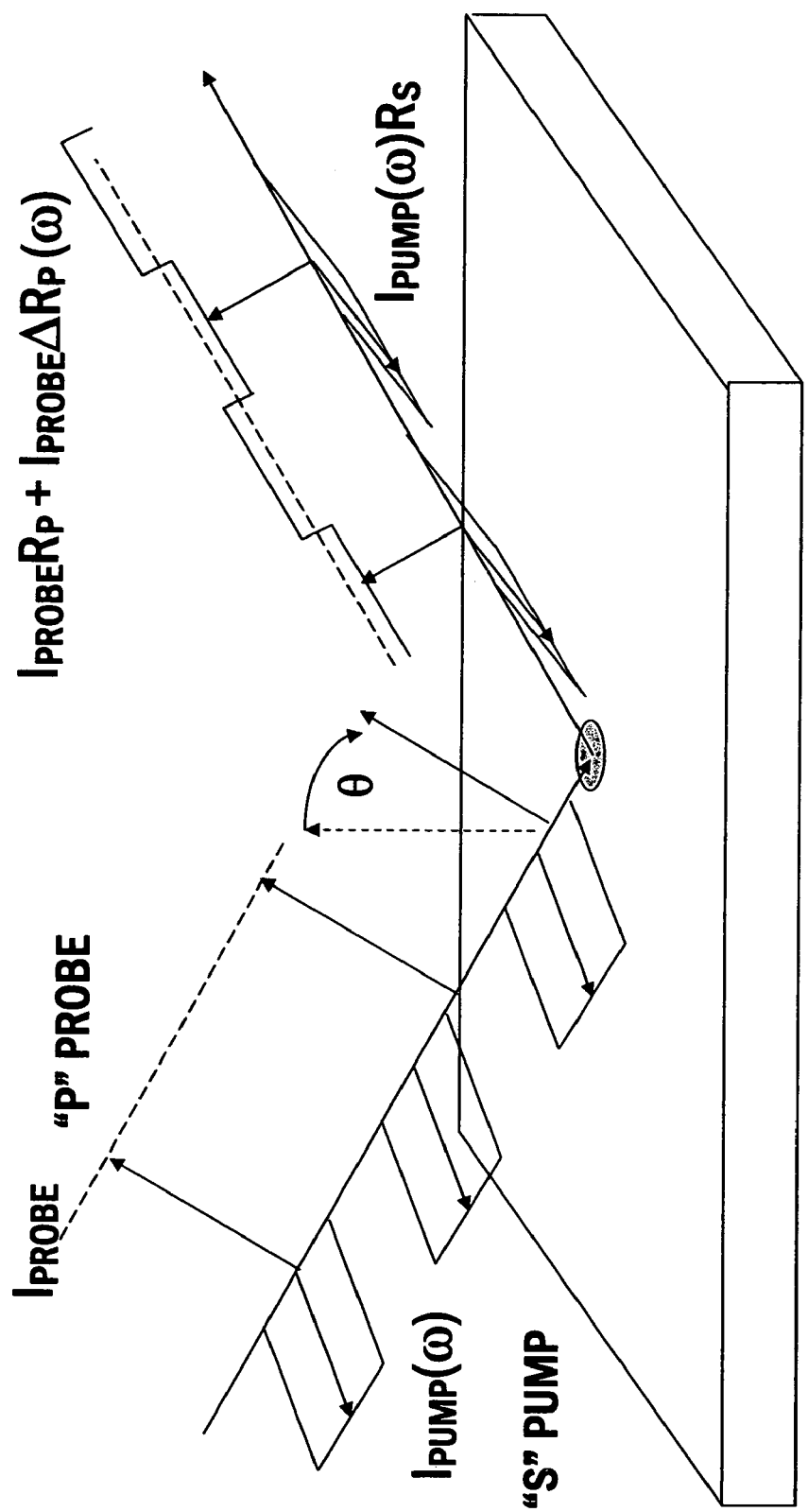
FIG. 4 is a schematic representation of the polarization state at a sample.
Figure 5:
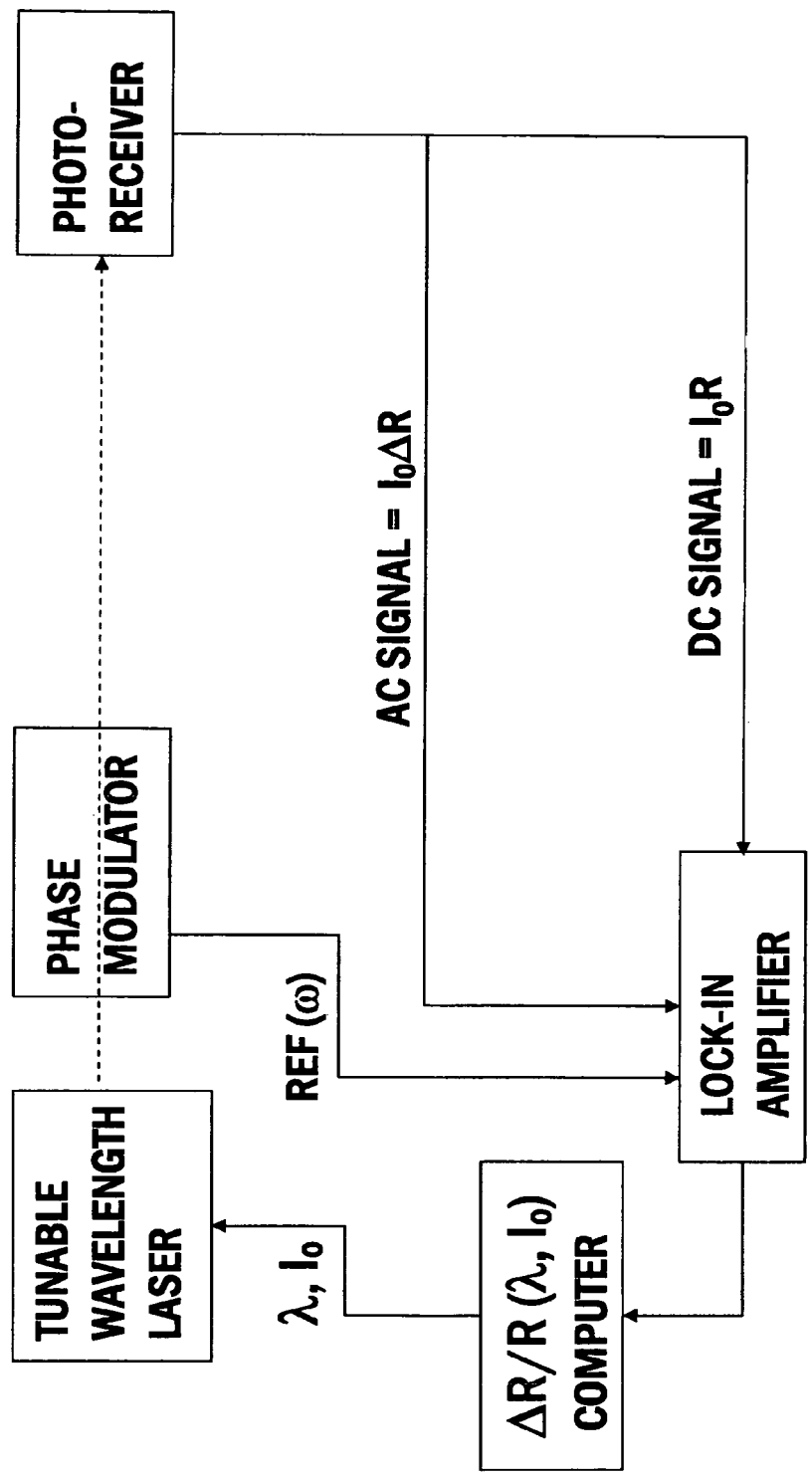
FIG. 5 is a block diagram of the electronic signals of a polarization modulation photo-reflectance apparatus.

As an exemplary mode of operation, the amplitude modulated pump beam is directed onto the sample with polarization parallel to the plane of incidence, also known as "p" polarization. The "p" orientation of the pump allows the reflected pump intensity to be minimized by placing the pump angle of incidence near the Brewster angle. The probe beam then has polarization perpendicular to the plane of incidence, known as "s" polarization. The intensity of the "s" polarized probe light may be written: $I_S=I_{PROBE}R_S+I_{PROBE}\Delta R_S(\omega)$. Alternatively, the amplitude modulated pump beam may be directed onto the sample with "s" polarization. In this case, as shown in FIG. 4., the pump polarization is entirely in the plane of the electronic interface, producing a sharp optical response due to the acceleration of carriers in the interfacial plane. The intensity of the "p" polarized probe light then may be written: $I_P=I_{PROBE}R_P+I_{PROBE}\Delta R_P(\omega)$. In either arrangement, the $\Delta R$ terms contained in the probe beam are induced by changes in the semiconductor optical response (Aspnes, 1980; Shay, 1970). The reflected beam is collected and focused onto the photodiode. The lock-in amplifier divides photodiode AC output at the phase modulation frequency by the DC signal. The computer controls the laser wavelength and intensity and records the measurement photocurrents. Any linear reflectivity contribution to the AC signal is removed by a fit to the slowly varying linear reflectivity background. Thus $\Delta R/R$ is recorded as a function of laser wavelength and intensity. FIG. 5. contains a block diagram of the electronic signals of the polarization modulation photo-reflectance apparatus. Embodiments include alterations to the arrangement which do not alter the fundamental polarization modulation photo-reflectance signal. Embodiments also include any configurations where the photoreceiver AC signal contains a photo-reflectance signal due to changes in sample semiconductor optical response induced by the change in pump beam polarization state.

Figure 6:
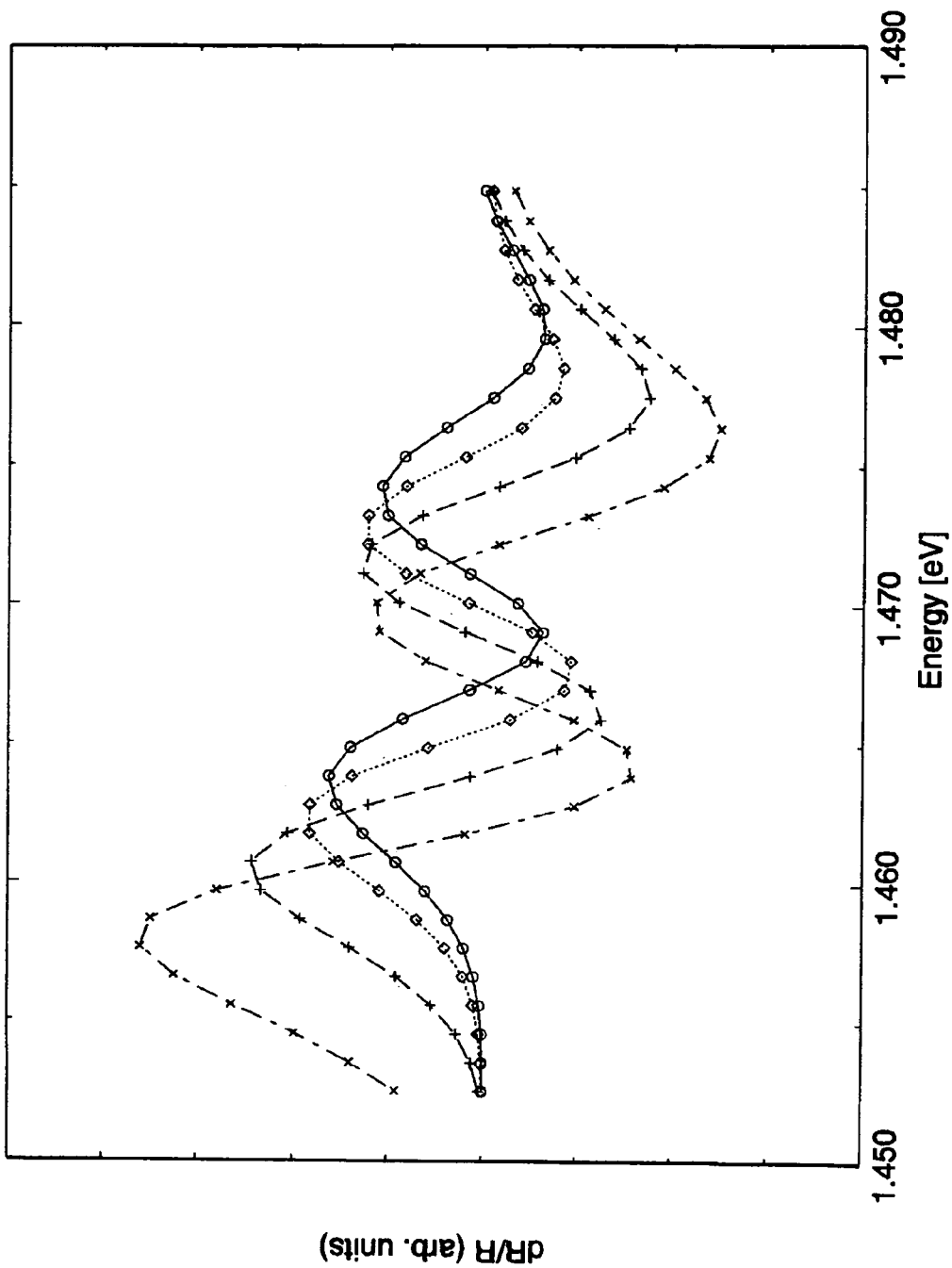
FIG. 6 is a graph of the photo-reflectance spectrum obtained from electronic interfaces as the laser intensity is increased.
Figure 7:
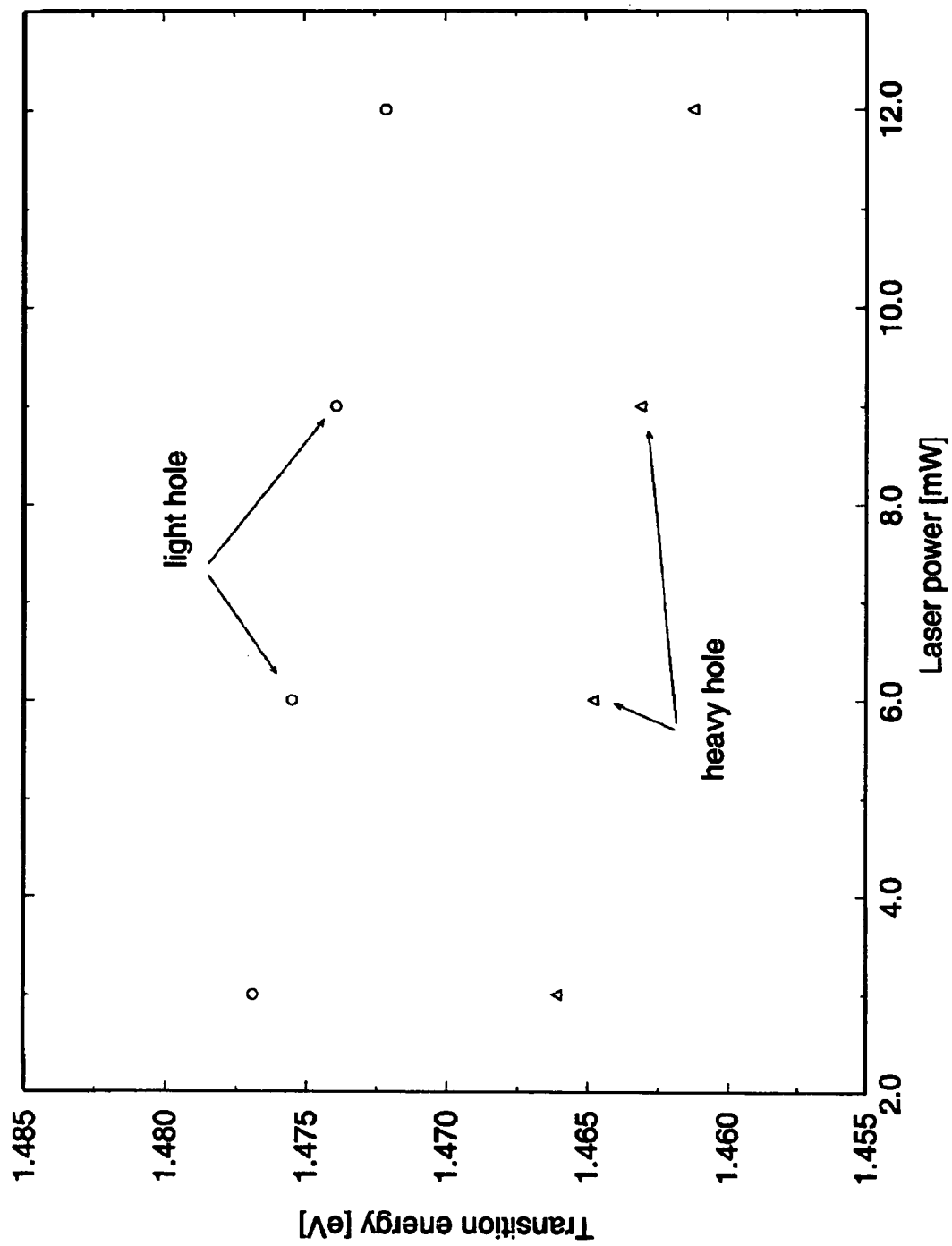
FIG. 7 shows redshifting of the band edge as laser intensity is increased.

The underlying principle of the polarization modulation photo-reflectivity technique is to characterize the photo-reflectance spectra associated with semiconductor electronic interfaces, and to derive critical point parameters associated with electronic interfaces such as excitonic resonance energies and spectral widths. Critical point parameters generally characterize the "active" electronic properties of electronic interfaces. Excitonic features are also enhanced in the presence of electronic confinement and characterize the splitting of the valence band. As is well known, the photoreflectance spectrum is proportional to a derivative of the dielectric function. The dielectric function of critical point and excitonic resonance features may be written:

$$\epsilon(E,\Gamma)=A\exp\{i\phi\}/(E-Eg+i\Gamma)^n,$$

where E is the photon energy, A is the oscillator amplitude, $\phi$ is the phase projection, Eg is the oscillator energy, $\Gamma$ is the broadening, and n is an exponent which characterizes the dimensionality of the resonance (Aspnes, 1980). Due to the dependence of electronic interface optical response on input polarization, amplitude analysis may be used to quantify anisotropies in the polarization modulation photo-reflectivity technique. However, the oscillator energy, Eg, and the spectral width, $\Gamma$, are the primary parameters of interest. Both Eg and $\Gamma$ may be determined simply from the lineshape of $\Delta R/R$ itself (Aspnes, 1980). The amplitude, broadening, and position of excitonic absorptions are strongly influenced by internal fields generated by photo-excited carriers. FIG. 6. illustrates photo-reflectance data from an electronic interface test structure exposed to a series of wavelength scans at laser powers of 3 mW, 6 mW, 9 mW, and 12 mW. The data is scaled with increasing laser power and curves are included to guide the eye. In these scans, the PMPR spectrum exhibits sharp derivative-like structures at interband transition energies. These nearby features indicate the valence band split into "heavy-hole" and "light-hole" bands, i.e. the degeneracy of the valence band is lifted. The ability to resolve such features is also important for the characterization of strain, since a primary effect of uniaxial stress is to split the valence bands. It is also seen that the relative amplitude of the lower energy transition increases with laser power, indicating a transfer of oscillator strength from the light hole to the heavy hole. Each curve is analyzed using the lineshape of $\Delta R/R$ (Aspnes, 1980), which reveals a redshift of the transition energies as laser intensity is increased. Transition energies derived from this data are shown in FIG. 7. The transition widths are essentially independent of laser intensity. The total redshift for either the light hole or the heavy hole transition is approximately 5 meV. For electronic interface test structure, redshifts due to space-charge separation of photo-excited carriers of approximately 1 meV per 6 kV/cm internal electric field are expected. Thus, the observed shifts are indicative of internal electric fields approximately 30 kV/cm in magnitude. Such fields can also be directly measured by photo-reflectance using the above bandgap Franz-Keldysh oscillations (Gray, 2001; Seraphin, 1965). However, the polarization modulation photoreflectivity technique provides a means to determine interfacial electric fields from line-shape analysis.

Figure 8:
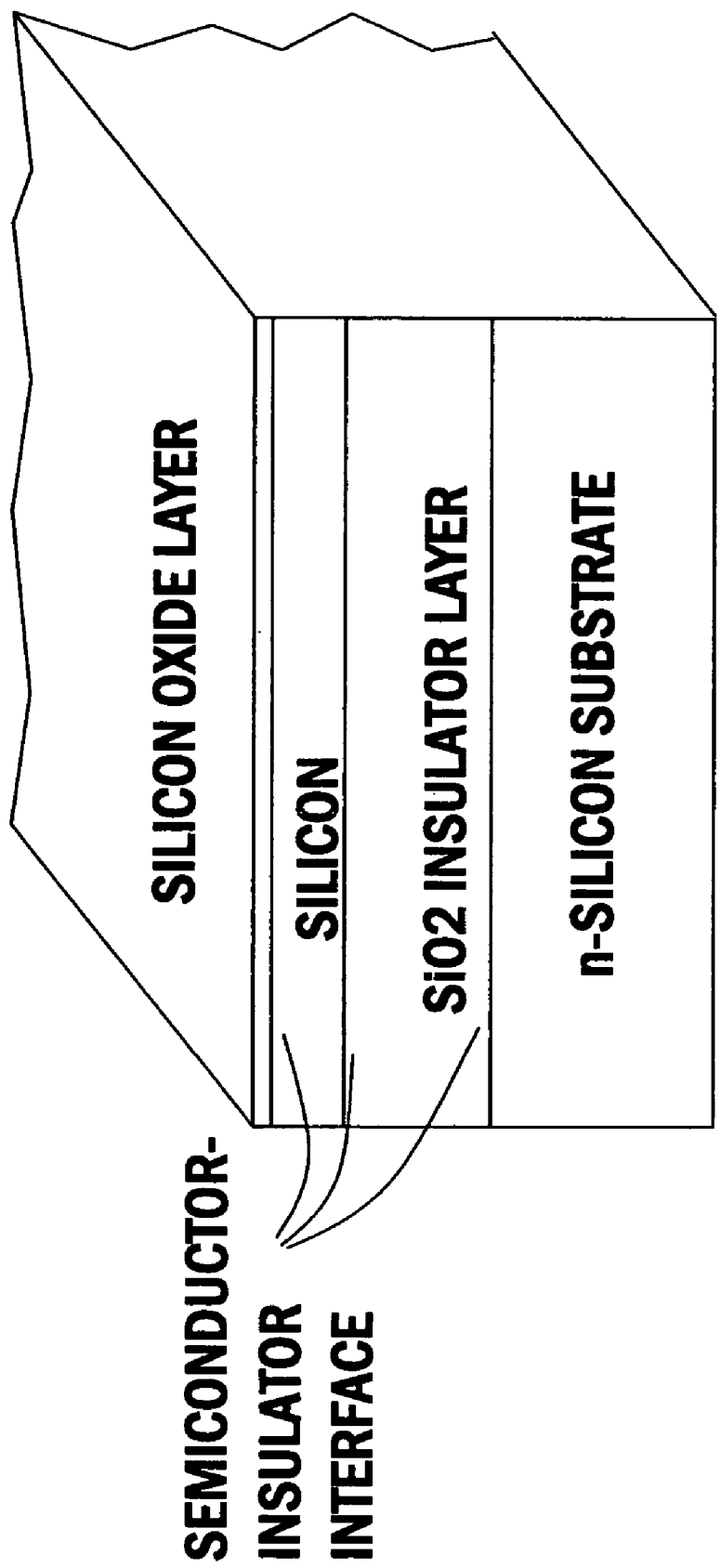
FIG. 8 illustrates an exemplary silicon semiconductor material containing electronic interfaces that may be analyzed using the photo-reflectance technique of the present disclosure.

In order to further teach the polarization modulation technique, FIG. 8 contains, in an exaggerated view, an exemplary silicon electronic interface test structure that may be characterized using the polarization modulation photo-reflectance technique of the present disclosure. The electronic interface test structure comprises a silicon semiconductor substrate upon which is grown a silicon dioxide "insulator" layer of ~87.1 nanometer thickness. An epitaxial silicon layer is bonded with the spacer layer, cleaved and re-grown to a thickness of approximately 25 nm. Then a silicon dioxide or high-K dielectric capping film of approximately 2 nanometer is grown.

Figure 9:
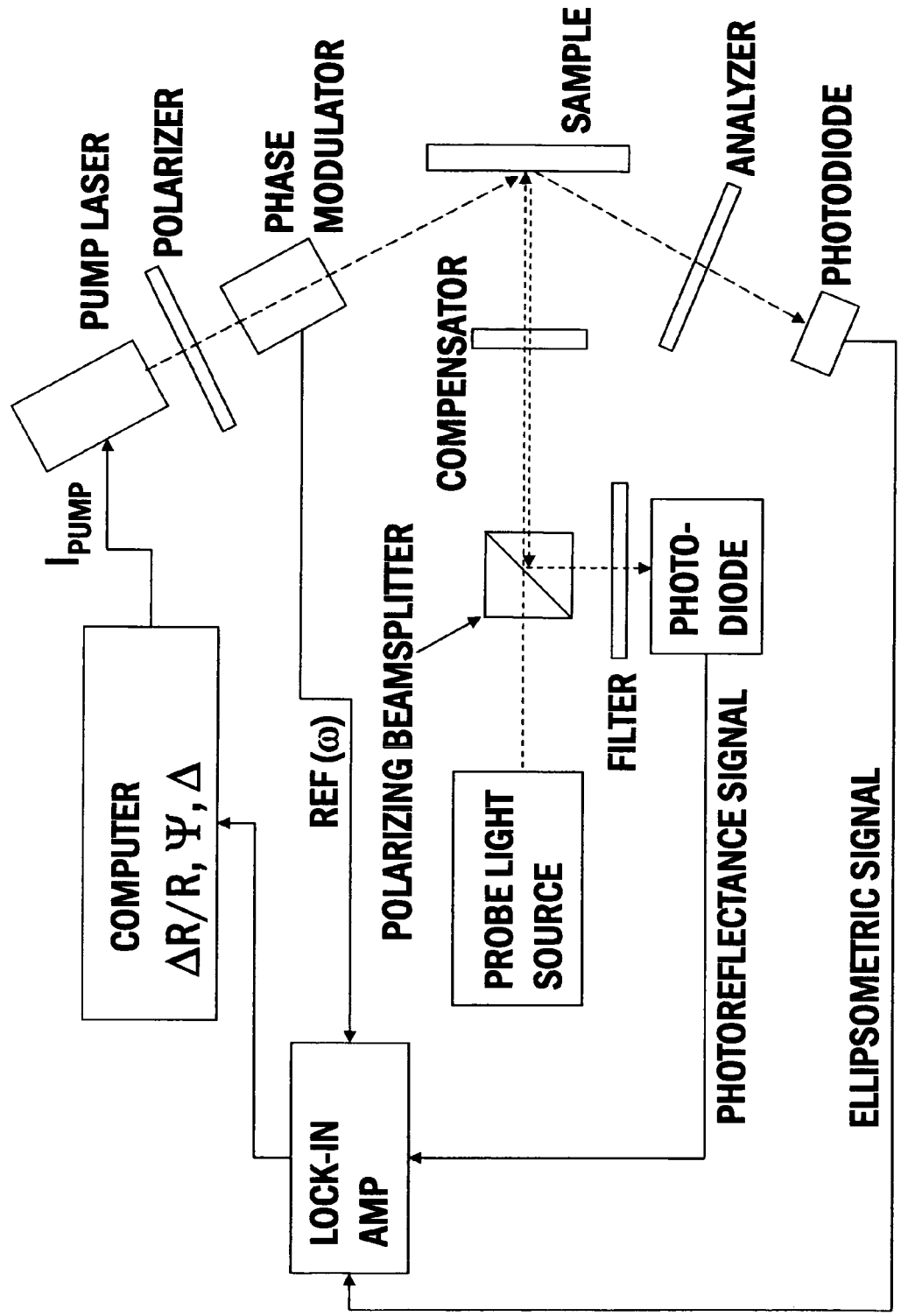
FIG. 9 contains an arrangement of a polarization modulation photo-reflectivity apparatus which may be used to provide polarization modulation photo-reflectance characterization in accordance with present disclosure.

In accordance with the arrangement of the present disclosure as shown in FIG. 9, polarization modulation photo-reflectance may be used to measure the reflected spectra from the electronic interface test structure in order to characterize the properties of the electronic interface and to establish the form of the dielectric function in the vicinity of critical points of silicon semiconductor material. As shown in FIG. 9, a preferred polarization modulation photo-reflectance arrangement comprises a pump diode laser, a laser controller, a polarizer, a phase modulator driven by an external function generator, a sample, an analyzer, a probe light source, a polarizing beamsplitter, a compensator, a pump wavelength filter, pump and probe optical systems, photodiodes, a lock-in amplifier, and a computer with measurement and system control software.

Figure 10:
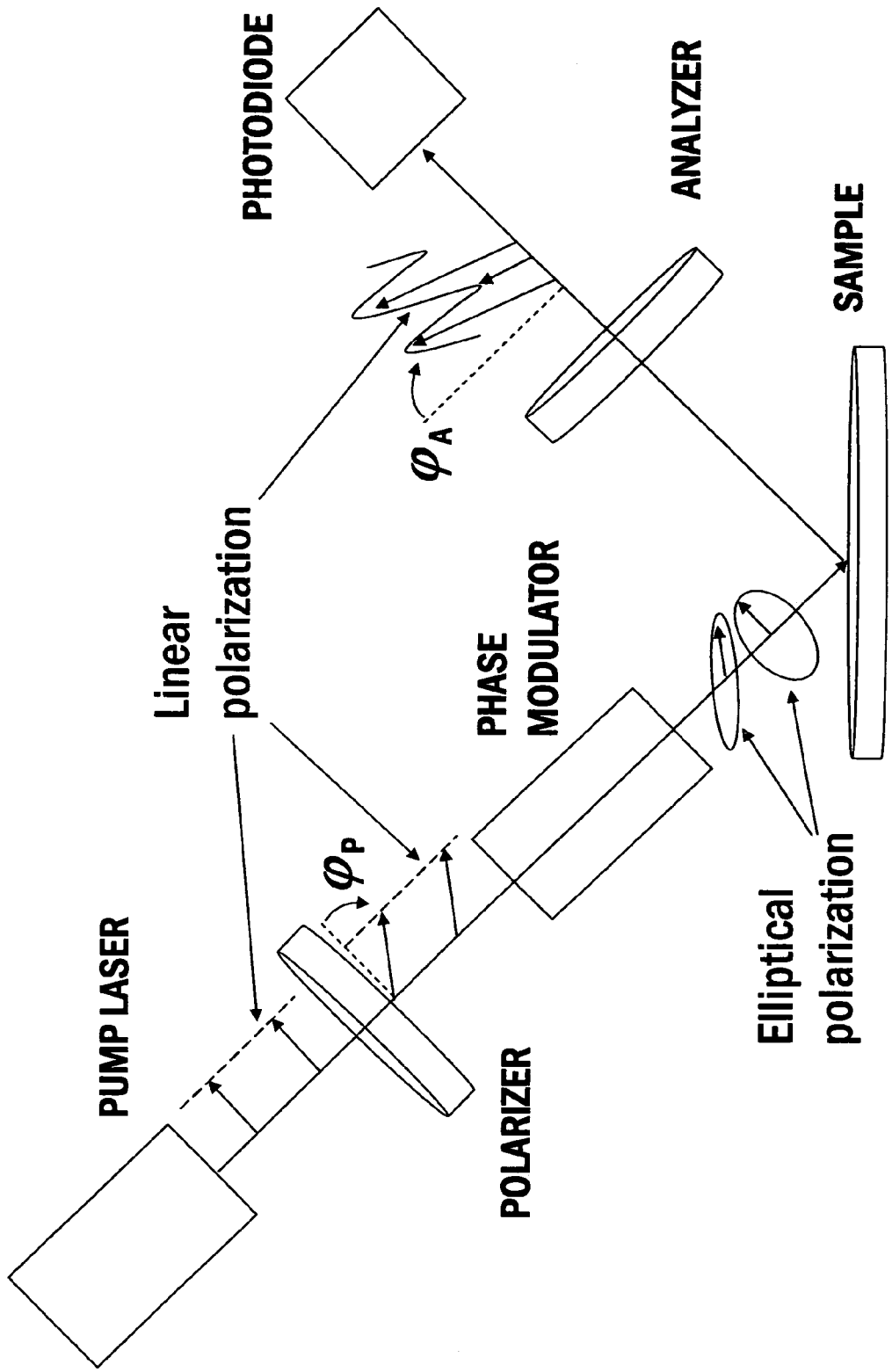
FIG. 10 is a schematic representation of a pump polarization state through an optical system.

The pump source is preferably a diode laser with center wavelength of approximately 844 nm. Preferred laser embodiments include diode lasers emitting in the UV-NIR wavelength range (200-1700 nm). The laser power is approximately 15 mW. However, laser embodiments may also include lasers operating at powers of approximately 0.5 mW or above. The laser controller is a programmable power source compatible with the laser diode and may be controlled by the computer. The pump beam is directed through a polarizer to the phase modulator where its polarization state is modulated. In an exemplary embodiment the phase modulator has a resonant frequency of approximately 20 MHz and is driven by an external function generator. Preferred embodiments also include broadband phase modulation, including DC bias operation, and photo-elastic modulation. The probe light source is a diode laser with center wavelength of approximately 375 nm. This wavelength is at or very near the strong silicon "E1" direct interband transition. The pump and probe are made coincident of the sample. The optical system comprises various optical elements including focusing and collimation lenses, and mirrors. The beam containing the polarization modulated pump is focused onto the sample surface at an angle of incidence of approximately 65°. Once the pump beam is reflected from the sample surface, it has sources of amplitude modulation from the differential reflectivity of the "s" and "p" polarizations, and from any induced change in the semiconductor optical response. The pump beam is configured as an ellipsometer with a polarization analyzer placed in the path of the reflected beam (Jellison, 2001). FIG. 10 shows the polarization state of the pump beam as it passes through the pump optical system. In an exemplary embodiment, the first polarizer is set to 45° degrees with respect to the plane of incidence, $\phi_P = 45°$, the azimuthal angle of the phase modulator is aligned with the plane of incidence, and the polarization analyzer is set to 45° with respect to the angle of incidence, $\phi_A = 45°$. The intensity of the polarized pump then is:

$$I = I_0 R/4 \times \{1 + S \times \sin[A\sin(\omega t)] + C \times \cos[A\sin(\omega t)]\},$$

where the amplitudes S and C are the isotropic Mueller matrix elements related to the ellipsometric parameters $\Psi$ and $\Delta$ through the relation:

$$S = \sin(2\Psi)\sin(\Delta), \quad C = \sin(2\Psi)\cos(\Delta).$$

Figure 11:
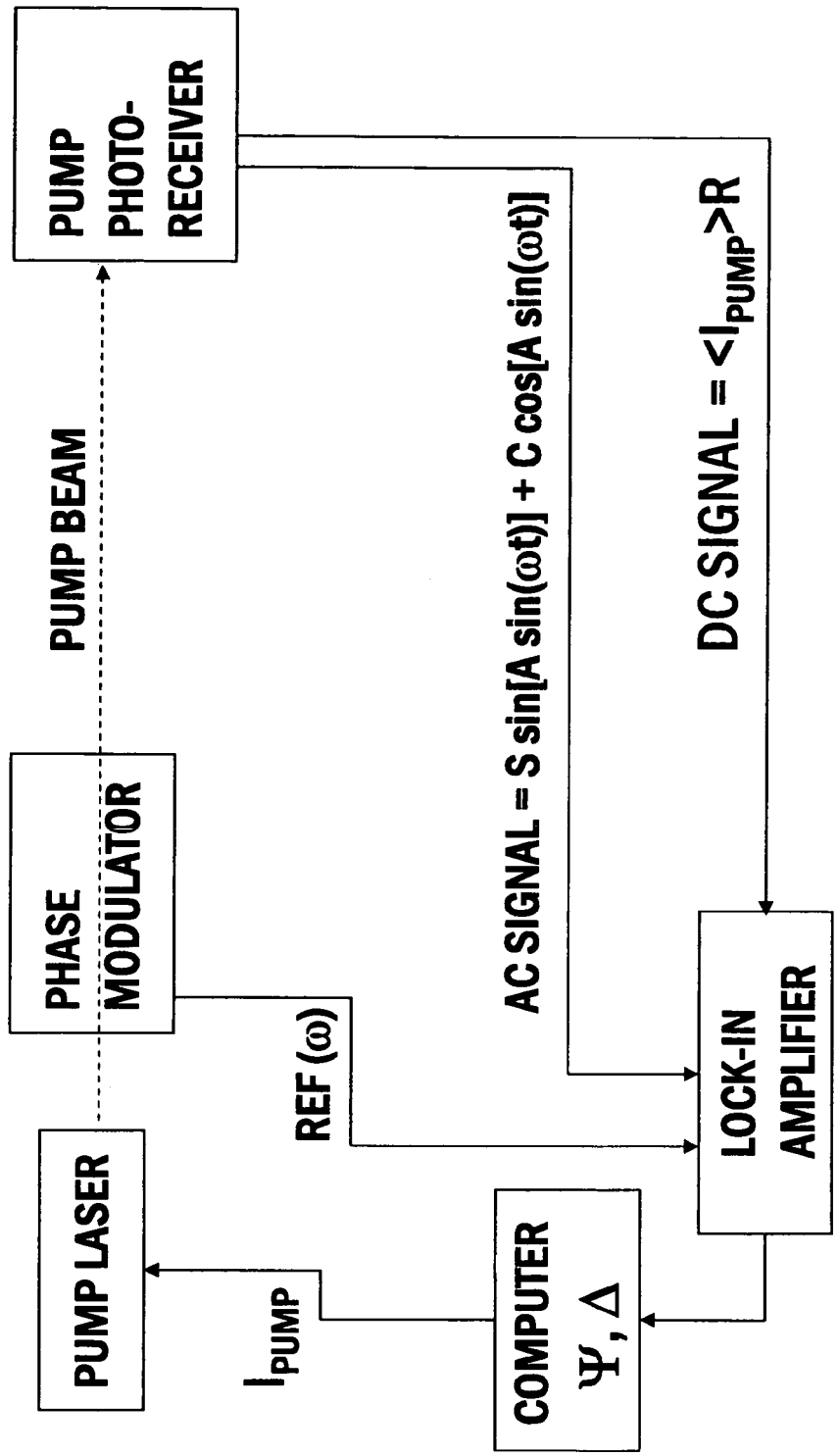
FIG. 11 is a block diagram of the electronic signals of a pump system.

Thus, the ellipsometer is configured to be sensitive to the ellipsometric parameter $\Delta$ irrespective of its value. This is important for the characterization of ultra-thin films, since, for such films, the optical thickness is proportional to the parameter $\Delta$. FIG. 11 shows a block diagram of the electronic signals associated with the pump/ellipsometer system. The pump laser beam is directed through the phase modulator to generate polarization state modulation, onto the sample, and to an analyzer which converts the signal to amplitude modulation. The optical system supplies an amplitude modulated light beam to the photoreceiver. The photoreceiver generates a photocurrent proportional to the intensity. This signal and the reference signal from the phase modulator are input to the lock-in amplifier. The lock-in amplifier divides photodiode AC output at the phase modulation frequency by the DC signal. The computer controls the pump laser intensity and records the measurement photocurrents. Thus the ellipsometric parameters $\Psi$ and $\Delta$ may be recorded as a function of pump wavelength and intensity.

Figure 12:
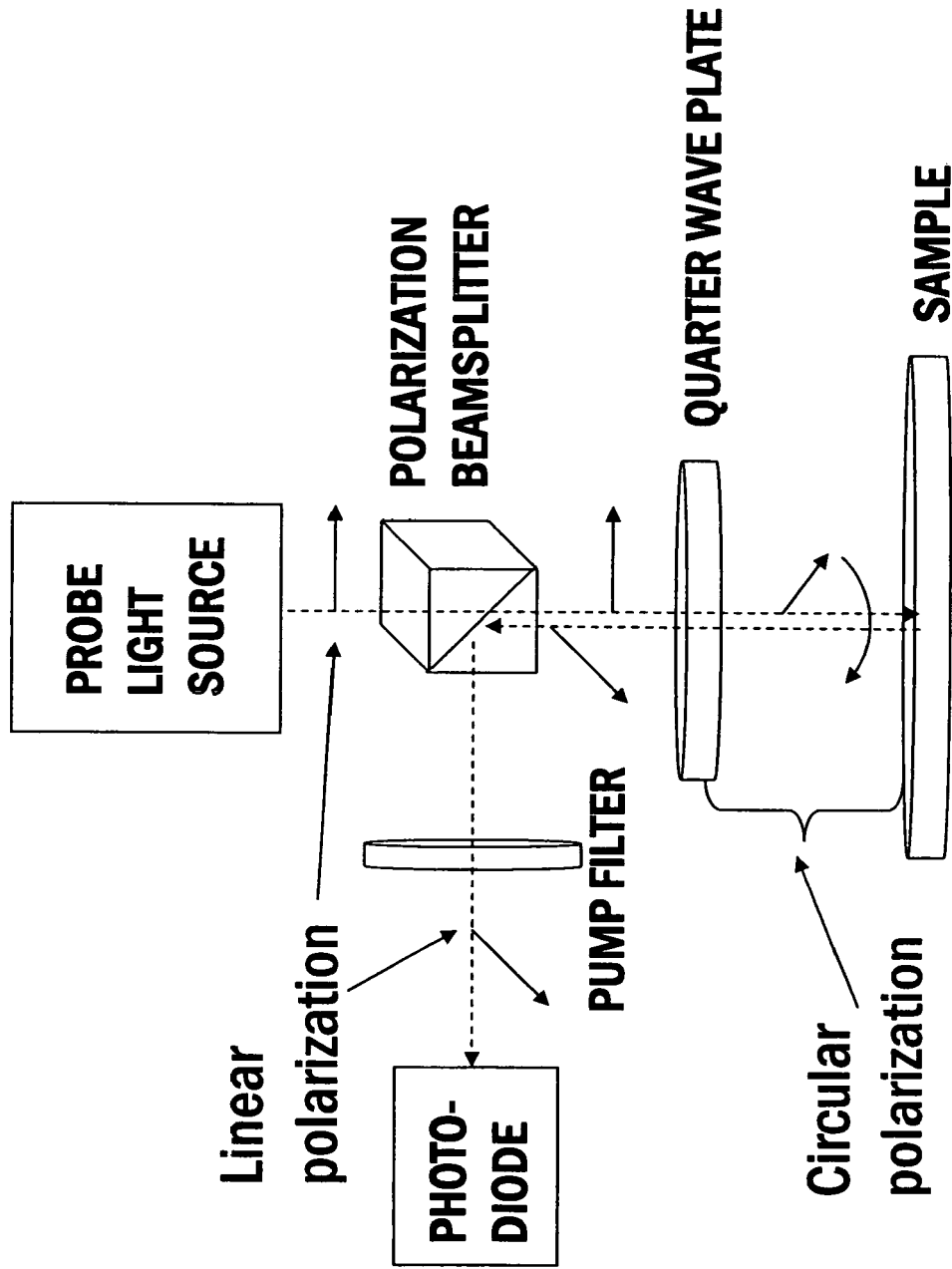
FIG. 12 is a schematic representation of a probe polarization state through an optical system.
Figure 13:
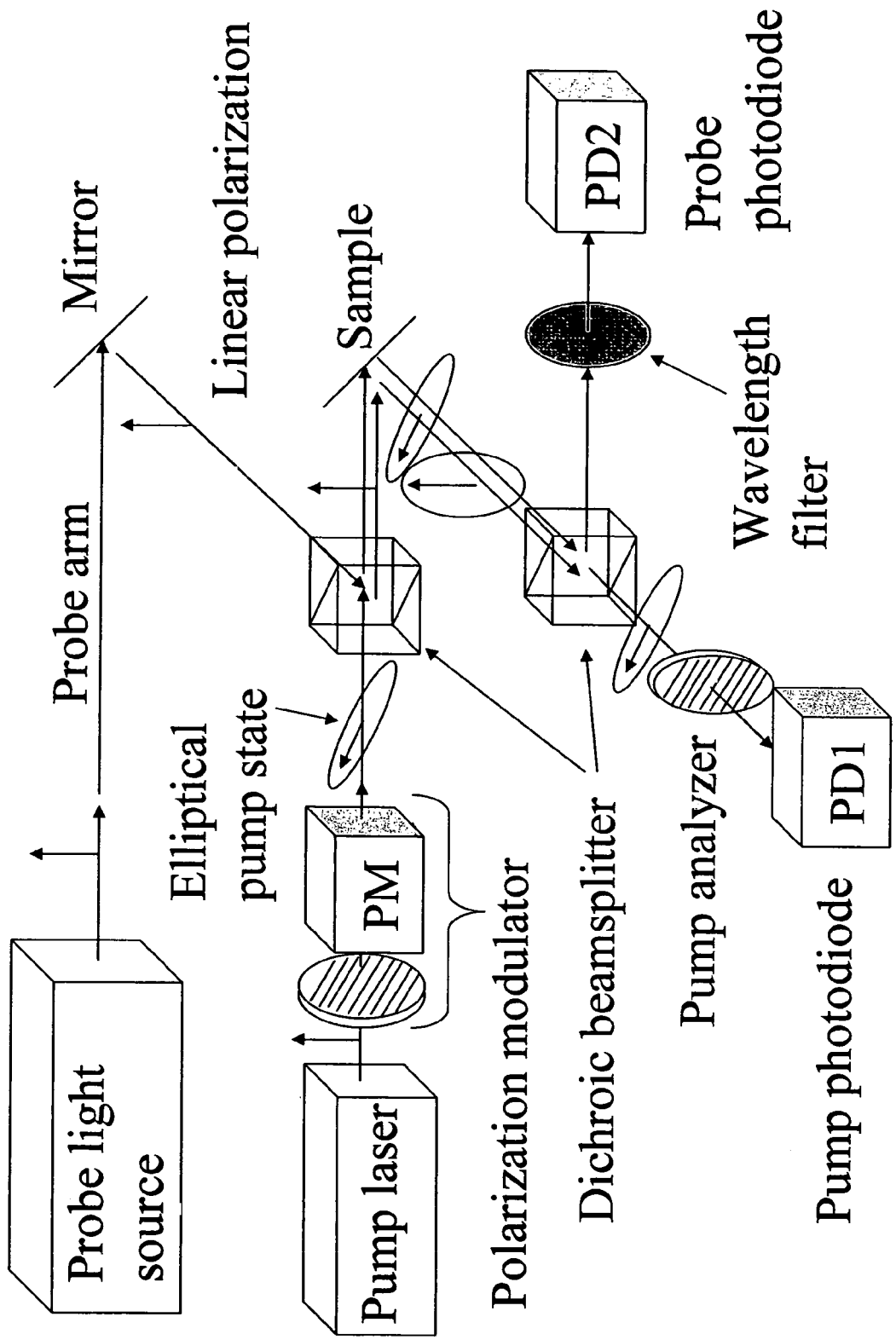
FIG. 13 is a schematic representation of a pump and probe polarization state through an optical system.
Figure 14:
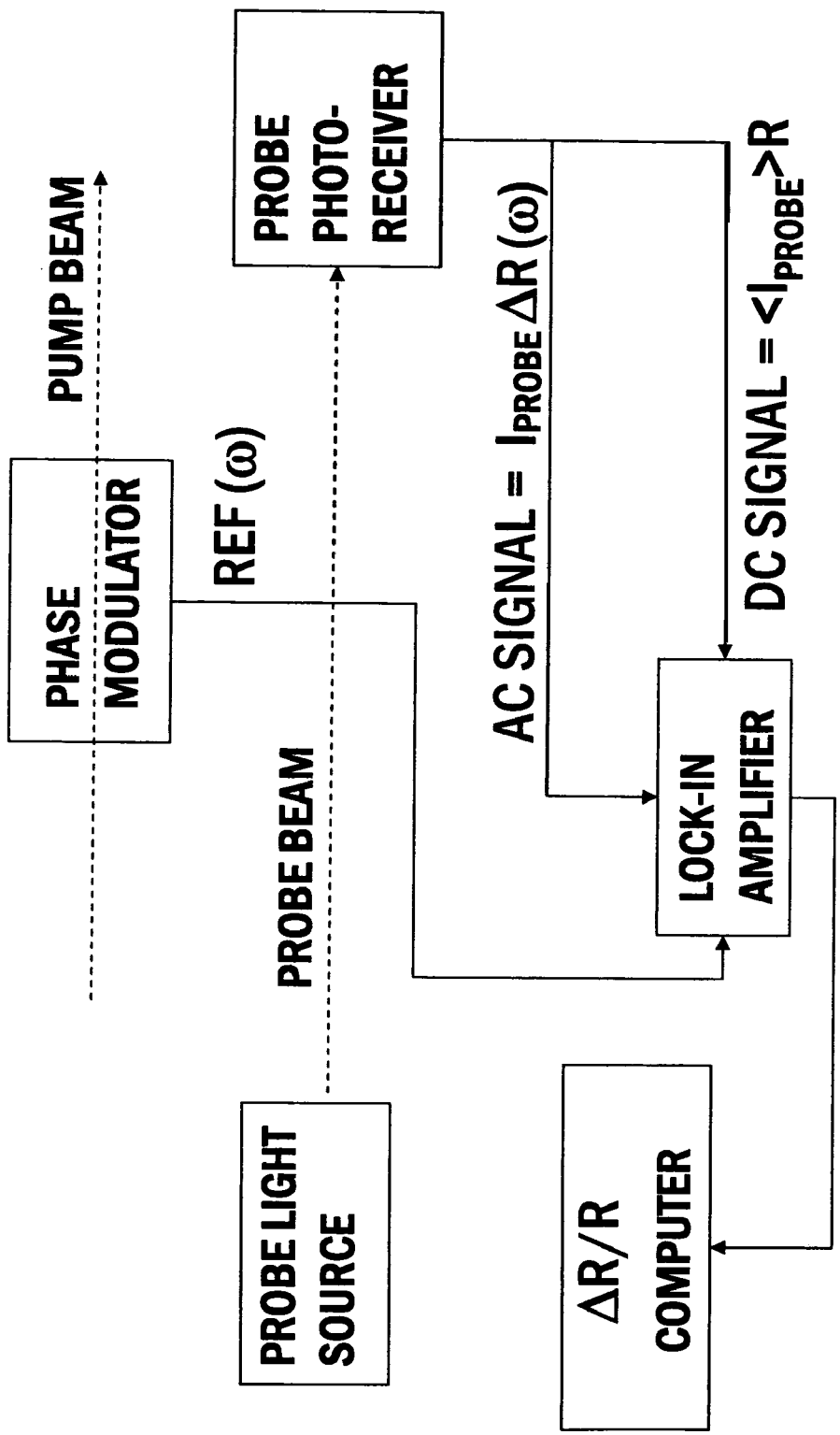
FIG. 14 is a block diagram of the electronic signals of a probe system.

As an exemplary mode of operation a normally incident probe laser source can be spatially overlapped with the pump beam at the sample. FIG. 12 shows the polarization state of the probe beam as it passes through the probe optical system. The normally incident probe beam passes through a polarization beamsplitter and quarter wave plate to the sample, and returns through the wave plate to the beamsplitter with a 90° polarization rotation about the optical axis. The beamsplitter directs this rotated polarization light to a photodiode. Any light from the pump may also be eliminated with a wavelength filter. In other embodiments, the probe beam is separated from the pump through the use of a dichroic beamsplitter and/or a wavelength filter. FIG. 13 shows the polarization state of the pump and the probe beams through an optical system with such a collinear beam arrangement. The linearly polarized probe may be transmitted to the photodiode without polarization elements. The probe light source may also be unpolarized. The probe beam has amplitude modulation only from pump induced changes in the semiconductor optical response (Aspnes, 1980; Shay, 1970). The reflected beam is collected and focused onto the photodiode. FIG. 14 contains a block diagram of the electronic signals associated with the probe system. The pump laser beam is directed through the phase modulator to induce modulation of the sample optical response. The probe beam contains the modulated reflectivity of the sample. The optical system supplies the amplitude modulated probe light beam to the photoreceiver. The photoreceiver generates a photocurrent proportional to the intensity. This signal and the reference signal from the phase modulator are input to the lock-in amplifier. The lock-in amplifier divides photodiode AC output at the phase modulation frequency by the DC signal. The computer controls the laser intensity and records the measurement photocurrents. Thus $\Delta R/R$ is recorded as a function of probe wavelength and pump intensity. Preferred embodiments include alterations to the arrangement which do not alter the fundamental polarization modulation photo-reflectance signal. Certain embodiments also include any configurations where the photoreceiver AC signal contains a photo-reflectance signal due to changes in sample semiconductor optical response induced by the change in pump beam polarization state.

Figure 15:
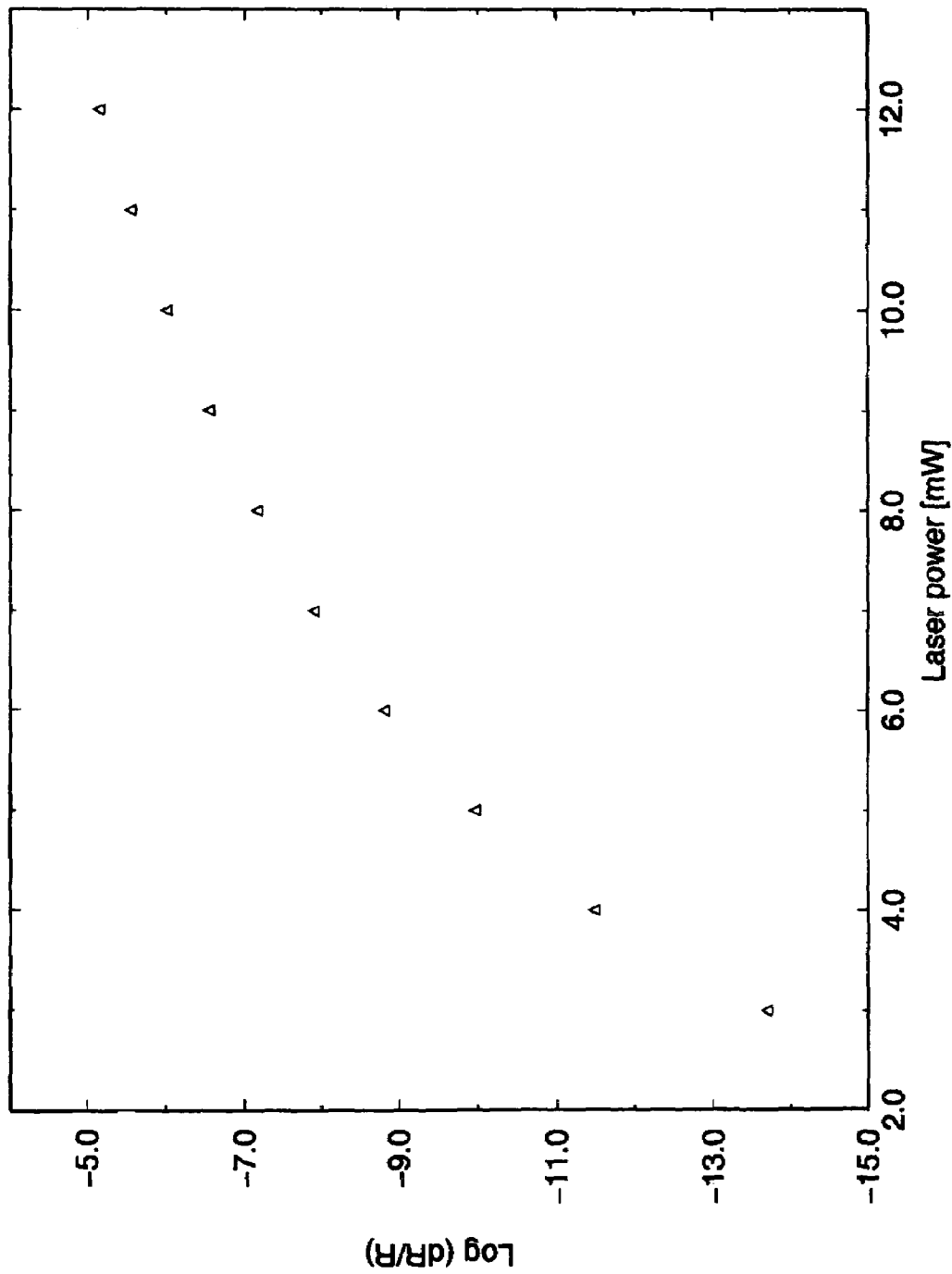
FIG. 15 is a graph of a photo-reflectance spectrum obtained from electronic interfaces as the laser intensity is increased.

As discussed, the underlying principle of the polarization modulation photo-reflectivity technique is to characterize the photo-reflectance spectra associated with semiconductor electronic interfaces, and to derive critical point parameters associated with electronic interfaces such as interband transition energies. Critical point parameters generally characterize the "active" electronic properties of electronic interfaces. Absorption features near critical points are enhanced in the presence of an electric field. The optical absorption at energies just below the critical point energy depends on the electric field amplitude and direction and may be written:

$$\alpha(F) = C \times F^2 \exp\{-K/F\},$$

where C and K are constants which depend on the "zero field" absorption, the effective electronic mass, and difference in photon energy from the strong absorption feature. The "zero field" absorption is the optical absorption of the material wherein no electric field is applied, and may be anisotropic. The effective mass is the mass along the direction of the applied field and also may be anisotropic. The expression above describes the redshifting of an optical absorption edge in the presence of a strong electric field (Keldysh, 1958). The change in absorption induces a simultaneous change in refractive index. These are manifest in the photoreflectance data though the relation:

$$\Delta R/R = \alpha \Delta \epsilon_1 + \beta \Delta \epsilon_2,$$

where $\Delta \epsilon_1$ and $\Delta \epsilon_2$, are the change in real and imaginary parts of the dielectric function, and $\alpha$ and $\beta$ are the Seraphin coefficients (Xiang, 1988, Seraphin, 1965). Due to the dependence of interfacial electric fields on input polarization, amplitude analysis may be used to quantify the electric field (Pollack, 1994, Aspnes, 1980). FIG. 15. illustrates photo-reflectance data from an electronic interface test structure exposed to a power scan of the pump laser from 3 mW to 12 mW. The data shows the natural logarithm of the probe photoreflectance signal at 375 nanometer wavelength with increasing pump laser power. The amplitude of the photoreflectance signal increases from approximately $1.13 \times 10^{-6}$, to approximately $5.83 \times 10^{-3}$, over this power interval. Analysis of the amplitude according to the Keldysh expression indicates internal electric fields in the range of 15-30 kV/cm. Thus, the polarization modulation photoreflectance technique provides a means to determine interfacial electric fields from amplitude analysis.

Thus, this disclosure is suitable for the characterization of polarization modulated photo-reflectance as a function of pump intensity and probe wavelength. A diode laser focused onto the semiconductor material provides the optical intensity needed to induce changes in the optical response of semiconductor electronic interfaces due to space-charge separation of electrons and holes. The laser controller provides intensity control for the laser and, in the case of a tunable laser, the controller also provides wavelength control. The computer may program power and wavelength scans via interface to the laser controller. The phase modulator modulates the polarization state of the pump beam. An external function generator is used to provide AC drive current to the modulator. The probe light source may consist of a single wavelength laser, a tunable laser, or a lamp based source. The pump and probe beams are then spatially overlapped at a focal spot on the sample and reflected light is collected by the optical system. The probe beam is directed to a photoreceiver which generates an electrical current proportional to the input intensity. The photoreceiver output comprises the AC signal at the modulation frequency and the DC photocurrent. The AC signal is divided by the DC signal, which provides normalization of the probe light intensity. The AC signal is then proportional to the differential change in reflectivity. A lock-in amplifier with reference frequency from the phase modulator then conditions the photoreceiver signal. The computer records experimental photocurrents from the lock-in amp. Thus photoreflectance information related to the optical response of electronic interfaces is acquired. The ellipsometric information contained in the reflected pump beam may also be analyzed. After reflection from the sample, the polarization modulated pump beam is passed through a polarizer and directed to a photoreceiver which generates an electrical current proportional to the input intensity. The photoreceiver output comprises the AC signal at the modulation frequency and the DC photocurrent. The AC signal is a sum of odd and even harmonics of the phase modulation frequency. The amplitude of these harmonics contain the ellipsometric parameters $\Psi$ and $\Delta$. The AC signal is divided by the DC signal, which provides normalization of the pump intensity. A lock-in amplifier with reference frequency from the phase modulator then conditions the photoreceiver signal. The computer records experimental photocurrents from the lock-in amp. Thus ellipsometric information related to the optical response of semiconductor materials is acquired.

As to a further discussion of the manner of usage and operation of the present disclosure, the same should be apparent from the above description. Accordingly, no further discussion relating to the manner of usage and operation will be provided.

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

REFERENCES

U.S. Patent Documents:

| | | | |
|---|---|---|---|
| 6,195,166 | February 2001 | Gray | 356/477 |
| 4,931,132 | June 1990 | Aspnes | 156/601 |
| 3,982,207 | March 1975 | Dingle | 331/94.5 |

Other Publications:

"Physics of Optical Metrology of Silicon-Based Semiconductor Devices," J. E. Jellison, in *Handbook of Silicon Semiconductor Metrology*, edited by A. C. Diebold pp. 738 (Marcel-Dekker, New York, 2001).

"Nondestructive profile measurements of annealed shallow implants," P. Borden, et al., J. Vac. Sci. Technol. B 18, 602-604 (2000).

"Photomodulated reflectance study of InGaAs/GaAs/AlAs microcavity vertical-cavity surface emitting laser structures in the weak-coupling regime: The cavity/ground-state-exciton resonance," P. J. Klar et al., Phys. Rev. B 59, 2894 (1999).

"Room Temperature, Contactless Electromodulation Investigation of Wafer-Sized Quantum Well Laser Structures," F. H. Pollack et al., SPIE vol. 2693, pp. 455-466 (1996).

"Observation and analysis of epitaxial growth with reflectance-difference spectroscopy," D. E. Aspnes, Mater. Sci. Eng. B30, 109-119 (1995).

"Modulation Spectroscopy of Semiconductors and Semiconductor Microstructures," F. H. Pollack, in *Handbook on Semiconductors*, Vol. 2, edited by M. Balkanski, pp. 527-635 (North-Holland, Amsterdam, 1994).

"Photoreflectance study of photovoltage effects in GaAs diode structures," V. M. Airaksinen and H. K. Lipsanen, Appl. Phys. Lett. 60, 2110 (1992).

"Optical Properties of Ge-Si Superlattices," T. P. Pearsall, in *Electronic Properties of Multilayers and Low-Dimensional Semiconductor Structures*, edited by J. M. Chamberlain et al., pp. 375-397 (Plenum Press, New York, 1990).

"Photoreflectance and the Seraphin coefficients in quantum well structures," X. L. Zeng et al., SPIE vol. 946, pp. 43-47 (1988).

"Photoreflectance characterization of interband transitions in GaAs/AlGaAs multiple quantum wells and modulation-doped heterojunctions," O. J. Glembocki et al., Appl. Phys. Lett. 46, 970-972 (1985).

"Detection of thermal waves through optical reflectance," Allan Rosencwaig, Jon Opsal, W. Lee Smith, and D. L. Willenborg, Appl. Phys. Lett. 46, 1013-1015 (1985).

"Modulation Spectroscopy," D. Aspnes, in *Handbook on Semiconductors*, Vol. 2, edited by M. Balkanski, pp. 109 (North-Holland, Amsterdam, 1980).

"Polarization Effects in the Interband Absorption of Light in Semiconductors Subjected to a Strong Electric Field," L. V. Keldysh, O. V. Konstantinov, and V. I. Perel, Soviet Physics-Semiconductors 3, 876-884 (1970).

"Photoreflectance Line Shape at the Fundamental Edge in Ultrapure GaAs," J. L. Shay, Phys. Rev. B 2, 803-807 (1970).

"Franz-Keldysh Effect Above the Fundamental Edge in Germanium," B. O. Seraphin and R. B. Hess, Phys. Rev. Lett. 14, 138-140 (1965).

"THE EFFECT OF A STRONG ELECTRIC FIELD ON THE OPTICAL PROPERTIES OF INSULATING CRYSTALS," L. V. Keldysh, Sov. Phys. JETP 7 (34), 788 (1958).

The invention claimed is:

1. A method of determining physical characteristics of a semiconductor electronic interface, the method comprising the steps of:
    a) illuminating an area of a surface of a semiconductor material wherein the semiconductor material comprises one or more electronic interfaces with a wavelength tunable laser source having a center wavelength nearby to at least one critical point in the optical response of the semiconductor material, with a wavelength tuning range of approximately 15 nm or greater, and using a focal spot size of 50 microns or less, wherein the laser beam is split into separate pump and probe arms, the pump arm is passed through a phase modulator followed by a polarizer to achieve amplitude modulation of the pump beam, and the pump and probe beams are spatially overlapped prior to illuminating the semiconductor material;
    b) recording the reflected alternating current light from the illumination of the semiconductor material, wherein the alternating current light contains one of the photoinduced changes in the semiconductor optical response, known as the photoreflectance signal, and the difference in the linear reflectivity of the "p" and "s" components of polarization, known as the linear reflectance signal, or both;
    c) repeating steps a) and b) across the tuning range of the laser source of step a) so as to collect wavelength information in the vicinity of critical points in the optical response of the semiconductor material;
    d) repeating steps a) and b) across the power range of the laser source so as to collect intensity information in the vicinity of critical points in the optical response of the semiconductor material; and
    e) generating an output in visual or electronic format using the information collected in steps c) and/or d), wherein the output is indicative of one or more physical characteristics of the semiconductor material.

2. The method as defined in claim 1 wherein the electronic interfaces comprise semiconductor-dielectric interfaces, semiconductor-semiconductor interfaces, or mechanically strained semiconductor interfacial layers.

3. The method as defined in claim 1 wherein the pump and probe beams are made collinear prior to illuminating the semiconductor material.

4. The method as defined in claim 1 wherein the direction of polarization of the amplitude modulated pump light is approximately perpendicular to the direction of polarization of the probe light.

5. The method as defined in claim 1 wherein the direction of polarization of the amplitude modulated pump light is parallel to the pump beam plane of incidence onto the semiconductor material, known as "p" polarization.

6. The method as defined in claim 5, wherein the pump laser beam illuminates the semiconductor material at an angle of incidence at or near the Brewster angle, such that the reflected pump intensity is minimized.

7. The method as defined in claim 1, wherein the direction of polarization of the amplitude modulated pump light is perpendicular to the pump beam plane of incidence onto the semiconductor material, known as "s" polarization.

8. The method as defined in claim 5 wherein the pump light is filtered from the reflected alternating current light by the use of a polarizer oriented perpendicular to the direction of pump polarization.

9. The method as defined in claim 7 wherein the pump light is filtered from the reflected alternating current light by the use of a polarizer oriented perpendicular to the direction of pump polarization.

10. The method as defined in claim 1 wherein wavelength information is recorded related to an electronic interface and the linear reflectance spectrum is removed from the data using a fit to the linear reflectance background.

11. The method as defined in claim 1 wherein wavelength information is recorded related to critical points associated with semiconductor materials, and is used to derive critical point position, shape, amplitude, spectral width, and or phase parameter.

12. The method as defined in claim 1 wherein changes in critical point parameters as a function of pump beam intensity are determined.

13. Apparatus for detecting physical characteristic of a semiconductor electronic interface, comprising:
    a wavelength tunable diode laser;
    a laser controller effective to perform power and wavelength scans;
    a power supply connectable to supply power to the laser;
    a beamsplitter effective to separate the laser light beam into a first and a second beam;
    a phase modulator effective to produce modulation of the polarization state of the first or the second light beam from the laser to produce a polarization modulated light beam;
    a linear polarizer effective to produce amplitude modulated light from the polarization modulated light beam;
    an optical system effective to direct the first and the second light beams onto a sample and to direct light reflected from the sample into a photoreceiver;
    a photoreceiver configured to generate an electrical current proportional to the input intensity;
    a signal conditioner connected to record the photoreceiver output; and
    a computer with measurement and system control software.

14. The apparatus of claim 13, wherein the laser power is approximately 0.5 mW or greater with output wavelengths nearby to at least one critical point of a semiconductor material.

15. The apparatus of claim 13, wherein the polarization state modulator comprises an electro-optic phase modulator (EOM) or a photo-elastic phase modulator (PEM) driven by an external function generator.

16. The apparatus of claim 13, wherein the optical system comprises a polarizing beam splitter, a calcite polarizer, a quartz polarizer, and/or a magnesium fluoride polarizer.

17. A method of determining physical characteristics of a semiconductor electronic interface, the method comprising the steps of:
  a) illuminating an area of a surface of a semiconductor material wherein the semiconductor material comprises one or more electronic interfaces with a pump laser beam and a separate probe light beam, the probe beam containing at least one wavelength nearby a critical point in the optical response of the semiconductor material, and using a focal spot size of 50 microns or less, wherein the pump beam is passed through a phase modulator to achieve polarization state modulation of the pump beam, and the pump and probe beams are spatially overlapped prior to illuminating the semiconductor material;
  b) recording the reflected alternating current probe light from the illumination of the semiconductor material, wherein the alternating current probe light contains the photo-induced changes in the semiconductor optical response, known as the photoreflectance signal;
  c) recording the reflected alternating current pump light from the illumination of the semiconductor material, wherein the alternating current pump light contains the complex ratio of the linear reflectivity of the "p" and "s" components of polarization, known as the ellipsometry signal;
  d) repeating steps a) and b) across the power range of the pump laser so as to collect photoreflectance intensity information in the vicinity of critical points in the optical response of the semiconductor material; and
  e) generating an output in visual or electronic format using the information collected in steps b), c), and/or d), wherein the output is indicative of one or more physical characteristics of the semiconductor material.

18. The method as defined in claim 17 wherein the electronic interfaces comprise semiconductor-dielectric interfaces, semiconductor-semiconductor interfaces, or mechanically strained semiconductor interfacial layers.

19. The method as defined in claim 17 wherein the pump and probe beams are made collinear prior to illuminating the semiconductor material.

20. The method as defined in claim 17 wherein the pump light is separated from the reflected alternating current probe light by the use of a dichroic beamsplitter, a polarizing beamsplitter, or a wavelength filter.

21. The method as defined in claim 17, wherein the probe light source is spectroscopic, containing wavelengths nearby to at least one critical point in the optical response of the semiconductor material, with a wavelength range of approximately 15 nm or greater.

22. The method as defined in claim 17 wherein photoreflectance wavelength information is recorded related to critical points associated with semiconductor materials, and is used to derive critical point position, shape, amplitude, spectral width, and/or phase parameter.

23. The method as defined in claim 17 wherein changes in critical point parameters as a function of pump beam intensity are determined.

24. The method as defined in claim 17, wherein the pump laser beam illuminates the semiconductor material at an angle of incidence at or near the Brewster angle.

25. The method as defined in claim 17 wherein the pump beam is directed first through a polarizer, then through the phase modulator, onto the sample, through an additional polarizer, known as the analyzer, and finally onto a photoreceiver, such that the pump beam functions independently as a polarization modulation ellipsometer.

26. The method as defined in claim 25 wherein ellipsometry information is recorded related to semiconductor materials, and is used to derive film thickness or optical properties.

27. Apparatus for detecting physical characteristics of a semiconductor electronic interface, comprising:
  a pump laser beam;
  a laser controller effective to perform power scans;
  a power supply connectable to supply power to the laser;
  a linear polarizer effective to control the polarization angle of the pump beam;
  a phase modulator effective to produce modulation of the polarization state of the pump beam;
  a probe light source;
  an optical system effective to spatially overlap the pump and probe beam prior to illuminating the semiconductor material;
  a beamsplitter effective to separate the reflected pump and probe beams;
  a linear polarizer effective to analyze the polarization state of the reflected pump beam;
  an optical system effective to direct pump light reflected from a sample into a photoreceiver;
  a photoreceiver configured to generate an electrical current proportional to the pump intensity;
  a signal conditioner connected to record the pump photoreceiver output;
  an optical system effective to direct probe light reflected from a sample into a photoreceiver;
  a photoreceiver configured to generate an electrical current proportional to the probe intensity;
  a signal conditioner connected to record the probe photoreceiver output; and
  a computer with measurement and system control software.

28. The apparatus of claim 27, wherein the pump laser power is approximately 0.5 mW or greater.

29. The apparatus of claim 27, wherein the probe light beam is a laser beam containing at least one wavelength nearby to a critical point of a semiconductor material.

30. The apparatus of claim 27, wherein the probe light beam is a lamp based beam containing at least one wavelength nearby to a critical point of a semiconductor material.

31. The apparatus of claim 27, wherein the polarization state modulator comprises an electro-optic phase modulator (EOM) or a photo-elastic phase modulator (PEM) driven by an external function generator.

32. The apparatus of claim 27, wherein the optical system comprises a dichroic beam splitter, a polarizing beam splitter, and/or a wavelength filter.

* * * * *